US012616664B2

(12) United States Patent
Nembrini et al.

(10) Patent No.: US 12,616,664 B2
(45) Date of Patent: *May 5, 2026

(54) MYO-INOSITOL AND THE PREVENTION OF PRETERM BIRTH

(71) Applicant: SOCIETE DES PRODUITS NESTLE S.A., Vevey (CH)

(72) Inventors: Chiara Nembrini, Montpreveyres (CH); Irma Silva Zolezzi, Singapore (SG); Keith Malcolm Godfrey, Hampshire (GB); Wayne Cutfield, Auckland (NZ); Shiao-Yng Chan, Singapore (SG)

(73) Assignee: Societe des Produits Nestle S.A., Vevey (CH)

( * ) Notice: Subject to any disclaimer, the term of this patent is extended or adjusted under 35 U.S.C. 154(b) by 744 days.

This patent is subject to a terminal disclaimer.

(21) Appl. No.: 17/753,229

(22) PCT Filed: Aug. 21, 2020

(86) PCT No.: PCT/EP2020/073451
§ 371 (c)(1),
(2) Date: Feb. 24, 2022

(87) PCT Pub. No.: WO2021/037699
PCT Pub. Date: Mar. 4, 2021

(65) Prior Publication Data
US 2022/0287988 A1     Sep. 15, 2022

(30) Foreign Application Priority Data

Aug. 26, 2019    (EP) ..................................... 19193541
Jun. 22, 2020    (EP) ..................................... 20181466

(51) Int. Cl.
A61K 31/047     (2006.01)
A23L 33/125     (2016.01)
(Continued)

(52) U.S. Cl.
CPC .......... A61K 31/047 (2013.01); A23L 33/125 (2016.08); A23L 33/135 (2016.08);
(Continued)

(58) Field of Classification Search
CPC ................ A61K 31/047; A61K 9/0095; A61K 31/4415; A61K 31/525; A61K 31/593;
(Continued)

(56) References Cited

U.S. PATENT DOCUMENTS 8,404,690 B2    3/2013  Page et al.
2017/0020930 A1    1/2017  Ichim et al.

FOREIGN PATENT DOCUMENTS

CN        106573004 A    4/2017
CN        106794206 A    5/2017
(Continued)

OTHER PUBLICATIONS

Farren et al., "The Prevention of Gestational Diabetes Mellitus With Antenatal Oral Inositol Supplementation: A Randomized Controlled Trial", Diabetes Care, 2017, 40:759-763 (Year: 2017).*
(Continued)

*Primary Examiner* — Sahana S Kaup
*Assistant Examiner* — Joshua A Atkinson
(74) *Attorney, Agent, or Firm* — K&L Gates LLP

(57)            ABSTRACT

The present invention relates generally to the field of compositions comprising myo-inositol for use in the prevention of preterm birth and/or of conditions linked to preterm delivery in a female subject and/or in the offspring. The composition may be a nutritional composition, for example a maternal nutrition composition. The composition may be
(Continued)

| Ingredient | Amount per daily dose |
|---|---|
| Myo-inositol | 4g |
| Vitamin D | 10 µg |
| Vitamin B6 | 2.6 mg |
| Vitamin B12 | 5.2 µg |
| Vitamin B2 | 1.8 mg |
| Zinc | 10 mg |
| β-carotene | 720 µg |
| Folic acid | 400 µg |
| Iron | 12 µg |
| Calcium | 150 µg |
| Iodine | 150 µg |
| Lactobacillus rhamnosus GG[1)] | 1x10⁹ cfu |
| Bifidobacterium lactis BB12[2)] | 1x10⁹ cfu | specifically designed to provide optimized nutrition to a woman desiring to get pregnant or to a pregnant woman.

17 Claims, 6 Drawing Sheets

(51) Int. Cl.

| | |
|---|---|
| *A23L 33/135* | (2016.01) |
| *A23L 33/155* | (2016.01) |
| *A23L 33/16* | (2016.01) |
| *A61K 9/00* | (2006.01) |
| *A61K 31/4415* | (2006.01) |
| *A61K 31/525* | (2006.01) |
| *A61K 31/593* | (2006.01) |
| *A61K 31/714* | (2006.01) |
| *A61K 33/30* | (2006.01) |
| *A61K 35/00* | (2006.01) |
| *A61K 35/745* | (2015.01) |
| *A61K 35/747* | (2015.01) |

(52) U.S. Cl.
CPC ............. *A23L 33/155* (2016.08); *A23L 33/16* (2016.08); *A61K 9/0095* (2013.01); *A61K 31/4415* (2013.01); *A61K 31/525* (2013.01); *A61K 31/593* (2013.01); *A61K 31/714* (2013.01); *A61K 33/30* (2013.01); *A61K 35/745* (2013.01); *A61K 35/747* (2013.01); *A61K 2035/115* (2013.01)

(58) Field of Classification Search
CPC .... A61K 31/714; A61K 33/30; A61K 35/745; A61K 35/747; A61K 2035/115; A23L 33/125; A23L 33/135; A23L 33/155; A23L 33/16; A23L 33/15; A23V 2002/00; A61P 15/00
See application file for complete search history.

(56) References Cited

FOREIGN PATENT DOCUMENTS

| | | | | |
|---|---|---|---|---|
| NO | 03053447 | 7/2003 | | |
| WO | 2016020486 | 2/2016 | | |
| WO | 2016020491 | 2/2016 | | |
| WO | WO-2016020495 A1 * | 2/2016 | ............. | A23C 9/156 |

OTHER PUBLICATIONS

Santamaria et al., "Clinical and metabolic outcomes in pregnant women at risk for gestational diabetes mellitus supplemented with myo-inositol: a secondary analysis from 3 RCTs", American Jour of Obstetrics and Gynecology, 2018, vol. 219, issue 3, pp. 300.e1-300.e6 (Year: 2018).*

Crane et al., "Use of transvaginal ultrasonography to predict preterm birth in women with a history of preterm birth", Ultrasound Obstet Gynecol, 2008, 32: 640-645 (Year: 2008).*

Sae-Lin et al., "Incidence and risk factors of preterm premature rupture of membranes in singleton pregnancies at Siriraj Hospital", Obstetrics and Gynaecology Research, 2019, pp. 573-577 (Year: 2019).*

Mtagliano et al. "Inositol for the prevention of gestational diabetes: a systematic review and meta-analysis of randomized controlled trials" Archives of Gynecology and Obstetrics, 2019, vol. 299, pp. 55-68.

Godfrey et al. "Nutritional Intervention Preconception and During Pregnancy to Maintain Healthy Glucose Metabolism and Offspring Health ("NiPPeR"): study protocol for a randomised controlled trial" Trials, 2017, vol. 18, No. 1, 12 pages.

Plows et al. "Nutritional Supplementation for the Prevention and/or Treatment of Gestational Diabetes Mellitus" Current Diabetes Reports, 2019, vol. 19, No. 9, 15 pages.

Klein "Nutrient Requirements For Preterm Infant Formulas 1,2,3" J. Nutr., 2002, vol. 132, No. 6, pp. 1395S-1577S.

Yue, "Inositol Supplementation in Preterm Infants with RDS", International Journal of Pediatrics, vol. 01, Jan. 26, 1993, p. 54.

Office Action Received for Application No. CN202080061115.5, mailed on Aug. 1, 2023, 8 Pages of Official Copy.

Qiulan et al., " Analysis on Risk Factors, Placental Pathological Changes and Pregnancy Outcomes of Premature Rupture of Membranes", Maternal and Child Health Care of China, vol. 33, Issue No. 9, May 31, 2018, pp. 1981-1983.

Zehua et al., "Obstetrics and Gynecology", 1st Edition, Dec. 31, 2018, pp. 49-50.

Office Action Received forApplication No. CN202080061115.5, mailed on June 13, 2024, 8 Pages of Official Copy.

Zhang et al., "Association of Gestational Diabetes Mellitus and Abnormal Vaginal Flora With Adverse Pregnancy Outcomes", Medicine, 2018, vol. No. 97, Issue No. 34, 7 Pages.

Hallman et al., "Inositol During Perinatal Transition", Neoreviews, Feb. 2015, vol. No. 16, Issue No. 2, pp. e84-e93.

Moore et al.,"The Physiology of Fetal Membrane Rupture: Insight Gained From the Determination of Physical Properties", Placenta, Nov.-Dec. 2006, vol. No. 27, Issue No. 11-12, pp. 1037-1051.

Brazil Office Action for Appl No. BR1120220024126 dated Jun. 4, 2025, 5 pages

Lei et al., "Pregnancy Nutrition—At a Glance", Hebei Science and Technology Press, 2014, p. 389.

Maoqing, "Probiotics and Their Benefits", Scientific and Technical Documentation Press, 2018, p. 135-136.

Chinese Office Action for Appl No. 202080061115.5 dated Aug. 29, 2025, 6 pages.

* cited by examiner

Figure 1:

| Ingredient | Amount per daily dose |
|---|---|
| Myo-inositol | 4g |
| Vitamin D | 10 µg |
| Vitamin B6 | 2.6 mg |
| Vitamin B12 | 5.2 µg |
| Vitamin B2 | 1.8 mg |
| Zinc | 10 mg |
| β-carotene | 720 µg |
| Folic acid | 400 µg |
| Iron | 12 µg |
| Calcium | 150 µg |
| Iodine | 150 µg |
| Lactobacillus rhamnosus GG[1)] | $1 \times 10^9$ cfu |
| Bifidobacterium lactis BB12[2)] | $1 \times 10^9$ cfu |

Figure 2:

|  | Control (n=280) | Intervention (n=278) | Basic model OR (95% CI) | Adjusted model OR (95% CI) (N=511 with full dataset) |
|---|---|---|---|---|
| All Pre-labour ROM (preterm and term-onset) (PROM) (n=110) | 61/280 (21.8%) | 49/278 (17.7%) | 0.83 (0.59, 1.15) | 0.90 (0.64, 1.28) |
| Preterm-onset Pre-labour ROM (PPROM) (n=26) | 18/280 (6.4%) | 8/278 (2.9%) | 0.44 (0.20, 1.00) | 0.39 (0.16, 0.96) |

Figure 2bis:

|  | Control (n=280) | Intervention (n=277) | Basic model OR (95% CI) | Adjusted model OR (95% CI) (N=508 with full dataset) |
|---|---|---|---|---|
| All Pre-labour ROM (preterm and at term) (PROM) (n=110) | 61/280 (21.8%) | 49/277 (17.7%) | 0.83 (0.60, 1.16) | 0.93 (0.65, 1.32) |
| Preterm Pre-labour ROM (PPROM) (n=26) | 18/280 (6.4%) | 8/277 (2.9%) | 0.44 (0.20, 1.00) | 0.43 (0.17, 1.06) |

Figure 3:

| | Control | Intervention | Basic model Risk ratio (95% CI) | Adjusted model Risk ratio (95% CI) (N=508 with full dataset) |
|---|---|---|---|---|
| Preterm-onset PROM and preterm delivery (<37w) (n=21) | 16/280 (5.7%) | 5/277 (1.8%) | 0.32 (0.12, 0.85) | 0.23 (0.07 to 0.74; N=508) |

Figure 4

| | Control | Intervention | Basic model OR (95% CI) |
|---|---|---|---|
| Preterm Births Associated with Preterm Pre-labour ROM (n=10) (Spontaneous onset preterm labour) | 8/280 (2.9%) | 2/277 (0.7%) | 0.26 (0.06, 1.21) |
| Preterm Births Associated with Preterm Prelabour ROM (n=11) (Non-spontaneous onset preterm delivery) | 8/280 (2.9%) | 3/277 (1.1%) | 0.36 (0.1, 1.35) |

Figure 5:

| Incidence and relative risk of preterm delivery | Control | Intervention | Basic model Risk ratio / Mean difference (95% CI) | Fully adjusted model Risk ratio / Mean difference (95% CI) |
|---|---|---|---|---|
| Preterm delivery < 37 weeks (denominator all live births≥24 weeks); all study participants | 27/292 (9.2%) | 17/293 (5.8%) | 0.64 (0.35 to 1.14) | 0.48 (0.25 to 0.93, n=533) |
| Preterm delivery < 37 weeks (denominator all live births≥24 weeks); overweight/obese participants | 12/130 (9.2%) | 6/127 (4.7%) | 0.49 (0.19 to 1.30) | 0.24 (0.08 to 0.70, N=236) |

Figure 6

| Timing of delivery after PPROM | Control | Intervention |
|---|---|---|
| Preterm delivery < 37 wks | 16/18 (89%) | 5/8 (63%) |
| Term delivery ≥ 37 wks | 2/18 (11%) | 3/8 (37%) |

MYO-INOSITOL AND THE PREVENTION OF PRETERM BIRTH

CROSS REFERENCE TO RELATED APPLICATIONS

The present application is a National Stage of International Application No. PCT/EP2020/073451, filed on Aug. 21, 2020. which claims priority to European Patent Application No. 19193541.0, filed on Aug. 26, 2019, and European Patent Application No. 20181466.2, filed on Jun. 22, 2020, the entire contents of which are being incorporated herein by reference.

The present invention relates to the field of compositions comprising myo-inositol for use in the prevention of preterm birth and/or of conditions linked to preterm delivery in a female subject and/or in the offspring. The present invention also relates to the field of compositions comprising myo-inositol for use in the prevention of a preterm-onset pre-labour rupture of membranes (PPROM) and disorders and/or conditions linked thereto (including but not limited to preterm birth). The composition may be a nutritional composition, for example a maternal nutrition composition. The composition may be specifically designed to provide optimized nutrition to a woman desiring to get pregnant or to a pregnant woman.

Preterm birth (PTB) is defined as birth at <37 weeks of gestation or at <259 days since the first day of a woman's last menstruation, and it is broadly classified into extremely preterm (<28 weeks), very preterm (28 to <32 weeks), moderately preterm (32 to <34 completed weeks of gestation) and late PTB (LPTB, between 34 to <37 weeks of gestation.

PPROM is a pregnancy complication. In this condition, the amniotic membrane surrounding the baby ruptures prematurely. In humans, PPROM occurs before the 37th week of pregnancy. A PPROM can lead to an increased risk for infections. There is also a higher chance that the baby is born preterm before the 37th week of pregnancy.

PPROM happens in about 30% of preterm births. Prognosis is primarily determined by complications related to prematurity such as necrotizing enterocolitis, intraventricular hemorrhage, and cerebral palsy, as well as intrauterine infection.

Women who have had PPROM are usually at a higher risk of experiencing it again in future pregnancies. To the inventor's best knowledge, there is currently no recommended way to specifically prevent PPROM. Some have suggested that women with a history of preterm delivery, including those associated with PPROM, take progesterone supplementation to prevent a recurrence.

Generally, it is recommended that women take good care of themselves during pregnancy to prevent complications. Taking good care should include ensuring an optimal nutrition. In general, scientific evidence is accumulating that prenatal early nutrition causes programming of long-term health and well-being, and can impact the risk of developing chronic diseases. Several studies have shown that changes in dietary intake or manipulation of individual macro and micronutrients during the reproductive period can have an impact in several physiological processes, such as growth, metabolism, appetite, cardiovascular function among others (Koletzko B et al (2011) Am J Nutr 94(s):2036-435).

Therefore, nutritional status (nutrient stores and dietary intake) of women before and during pregnancy is of relevance to optimize neonatal and child health outcomes. Maternal nutrition is thought to affect the availability and supply of nutrients to the developing fetus that are required for critical developmental processes. Inadequate intakes of multiple micronutrients are common among women of reproductive age living in resource poor-settings (Torhem L E et al. (2010) J. Nutr. 140: 2051S-58S).

A large variety of nutrients have already been used in compositions for maternal administration and various nutritional compositions have been developed to address maternal nutrition needs. These typically contain vitamin and mineral mixes.

However, it would still be useful to specifically target the nutritional deficiencies of this specific population by selecting the most useful nutrients for these women such as to provide compositions tailored to the nutritional needs of women in the reproductive period to optimize the prenatal nutrition of mothers, for the benefit of the mother and of her infant.

In the absence of a recommended intervention specifically to contribute to the prevention of preterm birth, in particular when this is a consequence of a preterm-onset pre-labour rupture of membranes (PPROM), it would be desirable to have such an intervention available.

Further, a combination of optimal nutrition during pregnancy with a composition that is able to contribute to the prevention of preterm delivery, for example via prevention of preterm-onset pre-labour rupture of membranes (PPROM), would be desirable as well.

Any reference to prior art documents in this specification is not to be considered an admission that such prior art is widely known or forms part of the common general knowledge in the field.

Accordingly, there is a need to overcome one or more of the drawbacks of the prior art and/or to find a composition that can be used in the prevention of preterm delivery, for example via prevention of a preterm-onset pre-labour rupture of membranes (PPROM).

It would therefore be desirable to provide a composition for use in the prevention of preterm delivery, for example via prevention of a preterm-onset pre-labour rupture of membranes (PPROM), and/or of conditions linked to preterm delivery in a female subject and/or in the offspring; or at least to provide a useful alternative.

The objective of the present invention was it, hence, to enrich or improve the state of the art and in particular, to provide a compound and/or a composition for use in the prevention of preterm delivery, for example via prevention of a preterm-onset pre-labour rupture of membranes (PPROM), and/or of conditions linked to preterm delivery in a female subject and/or in the offspring.

Accordingly, there is also a need to overcome one or more of the drawbacks of the prior art and/or to find a composition that can be used in the prevention of a preterm-onset pre-labour rupture of membranes (PPROM) and disorders and/or conditions linked to PPROM in a female subject.

It would therefore be desirable to provide a composition for use in the prevention of a preterm-onset pre-labour rupture of membranes (PPROM) and disorders and/or conditions linked to PPROM in a female subject; or at least to provide a useful alternative.

The objective of the present invention was, hence, to enrich or improve the state of the art and in particular, to provide a compound and/or a composition for use in the prevention of a preterm-onset pre-labour rupture of membranes (PPROM) and disorders and/or conditions linked to PPROM in a female subject.

The inventors were surprised to see that the objects of the present invention could be achieved by the subject matter of the independent claims. The dependent claims further develop the idea of the present invention.

Accordingly, the present invention provides a composition comprising myo-inositol for use in the prevention of preterm delivery, for example via prevention of a preterm-onset pre-labour rupture of membranes (PPROM), and/or of conditions linked to preterm delivery in a female subject and/or in the offspring.

Accordingly, the present invention also provides a composition comprising myo-inositol for use in the prevention of a preterm-onset pre-labour rupture of membranes (PPROM) and disorders and/or conditions linked to PPROM in a female subject.

As used in this specification, the words "comprises", "comprising", and similar words, are not to be interpreted in an exclusive or exhaustive sense. In other words, they are intended to mean "including, but not limited to".

The present inventors were surprised to find that administering a composition comprising myo-inositol to pregnant women led to a statistically significant reduction in overall preterm births when adjustment was made for covariates including glycaemic status.

The present invention, hence, relates to a composition comprising myo-inositol for use in the prevention of preterm delivery and/or conditions linked to preterm delivery in a female subject and/or in the offspring. In a further aspect, the present invention relates the use of a composition comprising myo-inositol in the prevention of preterm delivery and/or conditions linked to preterm delivery in a female subject and/or in the offspring. The present invention further relates to a kit of parts comprising at least two physically separated compositions, each comprising at least one ingredient selected from the group consisting of from vitamin B2, vitamin B6, vitamin B12, and vitamin D, at least one of the physically separated compositions comprises myo-inositol and at least one of the physically separated compositions comprises probiotics, for use in the prevention of preterm delivery and/or conditions linked to preterm delivery in a female subject and/or in the offspring.

The present inventors were also surprised to find that by administering a composition comprising myo-inositol to pregnant women, the risk of PPROM could be significantly reduced, leading, for example, to a reduction of preterm delivery associated with PPROM. To the best knowledge of the inventors, this represents the first nutritional intervention that has been found to reduce the occurrence of PPROM. Without wishing to be bound by theory, the inventors currently believe that this effect is achieved through anti-inflammatory, metabolic and microbiome-related actions.

The present invention, hence, relates to a composition comprising myo-inositol for use in the prevention of a preterm-onset pre-labour rupture of membranes (PPROM) and disorders and/or conditions linked to PPROM in a female subject. In a further aspect, the present invention relates the use of a composition comprising myo-inositol in the prevention of a preterm-onset pre-labour rupture of membranes (PPROM) and disorders and/or conditions linked to PPROM in a female subject. The present invention further relates to a kit of parts comprising at least two physically separated compositions, each comprising at least one ingredient selected from the group consisting of from vitamin B2, vitamin B6, vitamin B12, and vitamin D, at least one of the physically separated compositions comprises myo-inositol and at least one of the physically separated compositions comprises probiotics, for use in the prevention of a of preterm-onset pre-labour rupture of membranes (PPROM) and disorders and/or conditions linked to PPROM in a female subject.

FIG. 1 shows the nutritional composition used on Example 1, 2

FIG. 2 and FIG. 2 bis shows the effect of the nutritional composition intervention on all Pre-labour Rupture of Membranes (PROM; occurring both at term and preterm) as well as on Preterm-onset Pre-labour Rupture of Membranes (PPROM) alone.

FIG. 3 shows an effect of the nutritional composition on Preterm-Onset Pre-labour Rupture of Membranes (PPROM) in preterm deliveries.

FIG. 4 shows lower incidence of preterm delivery associated with PPROM in the nutritional intervention group in both spontaneous and non-spontaneous preterm delivery groups.

FIG. 5 shows an effect of the nutritional intervention on reduction of the overall rate of preterm delivery in the whole study population as well as specifically in the overweight/obese subset, when adjusted for different covariates.

FIG. 6 shows that following the occurrence of PPROM, delivery was more likely to be at term than preterm (before 37 weeks) in the intervention group compared with the control group.

Consequently, the present invention relates in part to a composition comprising myo-inositol for use in the prevention of preterm delivery and/or conditions linked to preterm delivery in a female subject and/or in the offspring.

In one embodiment, the female subject is overweight and/or obese.

In another embodiment, the prevention of preterm delivery occurs via prevention of PPROM in a female subject.

Consequently, the present invention relates in part to a composition comprising myo-inositol for use in the prevention of a preterm-onset pre-labour rupture of membranes (PPROM) and disorders and/or conditions linked to PPROM in a female subject.

The term "prevent" or "prevention" as used herein refers to the prevention of the occurrence, or reduction of the risk of the occurrence, of an unwanted condition, disorder or conditions associated with such disorders in a female subject.

Within the context of the present invention, the term "Preterm birth (PTB)" or "preterm delivery" indicates birth at <37 weeks of gestation or at <259 days since the first day of a woman's last menstruation. Pre term birth can be broadly classified into extremely preterm (<28 weeks), very preterm (28 to <32 weeks), moderately preterm (32 to <34 completed weeks of gestation) and late PTB (LPTB, 34 to <37 weeks of gestation.

The term "subject" as used herein refers to a mammal and more particularly a cat, a dog or a human. The human may be a woman, for example, a woman who is trying to get pregnant, or who is pregnant. In an embodiment of the invention the subject is a mammal selected from the group consisting of a cat, a dog and, a human. For example, the subject may a woman who is trying to get pregnant, or who is pregnant.

Within the context of the present invention, the term "overweight" and/or "obese" means a subject having an elevated Body Mass Index (BMI) as defined by international classifications. In one embodiment, an Asian subject (including Chinese, Indians, Pakistani, Bangladeshi, Malay, mixed Asian) is overweight or obese if the subject has Body Mass Index (BMI)≥23 kg/m2. In another embodiment, a non-Asian subject (including White Caucasian, Polynesian, Black, mixed Asian-non-Asian) is overweight or obese if the subject has Body Mass Index (BMI)≥25 kg/m2.

Myo-Inositol, or cis-1,2,3,5-trans-4,6-cyclohexanehexol, is the predominant isomeric form of inositol. Myo-Inositol is a compound present in animal and plant cells and plays an important role in various cellular processes, as the structural basis for secondary messengers in eukaryotic cells, in particular as inositol triphosphates (IP3), phosphatidylinositol phosphate lipids (PIP2/PIP3) and inositol glycans. Myo-inositol has been shown to participate in a variety of biological process such as cell growth and survival, development and function of peripheral nerves, osteogenesis, energy metabolism and reproduction (Croze et al. (2013) Biochimie 95:1811-1827). Myo-inositol is found as free form, phosphoinositides and phytic acid, in fresh fruits and vegetables, and in all foods containing seeds (beans, grains and nuts) (Clements R S and Darnell B. Am J Clin Nutr (1980) 33:1954-1967). Myo-Inositol from phytic acid can be released in the gut by phytases found in plants, microorganisms and in animal tissues (Schlemmer U et al. Mol Nutr Food Res (2009) 53:S330-S375). These enzymes are capable of releasing free inositol, orthophosphate, and intermediary products including the mono-, di-, tri-, tetra- and penta-phosphate forms of inositol. Much of the ingested inositol hexaphosphate is hydrolysed to inositol. Myo-inositol is also commercially available from several suppliers.

Disorders and/or conditions linked to preterm delivery are known to the skilled artisan and include disorders and/or conditions which may affect both the newborn and the mother.

Preterm birth is associated for example with an increased risk of maternal mortality. Preterm birth is also a risk factor for adverse short and long-term health outcomes in the newborn. Short term, it is the leading cause of neonatal death and the second cause of all under 5 years mortality. Shorter term complications of prematurity include but are not limited to: increased risks of neonatal respiratory conditions (such as respiratory distress syndrome and bronchopulmonary dysplasia), necrotizing enterocolitis, sepsis, neurological conditions (such as periventricular leukomalacia, seizures, intraventricular hemorrhage, cerebral palsy, and hypoxic ischemic encephalopathy), as well as feeding difficulties and visual and hearing problems. Newborns born late preterm (34-<37 weeks) have significantly higher risks of adverse outcomes than term newborns. Preterm birth has been linked to poorer neurodevelopmental outcomes, higher rates of hospital admissions, as well as behavioral, social-emotional, and learning difficulties in childhood. It also leads to significant, long-term health systems costs as well as causes considerable psychological and financial hardship for the families of preterm newborns.

Long term, PTB it is associated with increased risks of hypertension, cardiovascular and cerebrovascular diseases, type 2 diabetes, chronic kidney disease, asthma and abnormalities in pulmonary function, and neurocognitive disorders. In addition, PTB is associated with increased health care costs and socioeconomic disadvantages in adulthood. For example, conditions linked to preterm birth in the new born may be selected from the group consisting of: increased risks of neonatal respiratory conditions (such as respiratory distress syndrome and bronchopulmonary dysplasia), necrotizing enterocolitis, sepsis, neurological conditions (such as periventricular leukomalacia, seizures, intraventricular hemorrhage, cerebral palsy, and hypoxic ischemic encephalopathy), feeding difficulties, visual and hearing problems, poor neurodevelopmental outcomes, high rates of hospital admissions, behavioral, social-emotional, and learning difficulties in childhood, increased risks of hypertension later in life, cardiovascular and cerebrovascular diseases later in life, type 2 diabetes later in life, chronic kidney disease later in life, asthma and abnormalities in pulmonary function, neurocognitive disorder and combinations thereof.

Disorders and/or conditions linked to PPROM are known to the skilled artisan. For example, the disorder and/or condition linked to a PPROM may be selected from the group consisting of premature birth; pulmonary hypoplasia in the newborn; infections, such as infections of the amniotic fluid and membranes, for example; the separation of the placenta from the uterus; complications with the umbilical cord; the necessity to deliver by surgical or cesarean section and combinations thereof.

Myo-Inositol may be administered in accordance with the present invention in any effective amount. Typically, an effective amount will depend on the type, age, size, health status, lifestyle and/or genetic heritage of the subject. The effective amount may be split into several smaller amounts and administered throughout the day so as the total daily intake is the effective amount. A person skilled in the art will be able to propose appropriate amounts of myo-inositol to be consumed per day. For example, the composition for use in accordance with the present invention may provide myo-inositol in an amount of 0.2 to 5 g, preferably 1.5 to 5 g, more preferably 2 to 5 g, most preferably 2 to 4 g per daily dose.

The composition used in the framework of the present invention may further comprise probiotics. It is particularly beneficial to combine myo-inositol with probiotics, as these have been found to improve the gut barrier function and to help nutrients pass through the gut (Cani P D et al. (2009) Gut 58:1091-1103). Combining myo-inositol with probiotics thus enhances the absorption of myo-inositol and other nutrients that may be present in the composition.

The term "probiotic" as used herein refers to live probiotic bacteria, non-replicating probiotic bacteria, dead probiotic bacteria, non-viable probiotic bacteria, fragments of probiotic bacteria such as DNA, metabolites of probiotic bacteria, cytoplasmic compounds of probiotic bacteria, cell wall materials of probiotic bacteria, culture supernatants of probiotic bacteria, and/or combinations of any of the foregoing. The probiotic may for example be live probiotic bacteria, non-replicating probiotic bacteria, dead probiotic bacteria, non-viable probiotic bacteria, or any combination thereof. In an embodiment of the invention the probiotic is live probiotic bacteria.

For example, the probiotics comprised in the composition used in the framework of the present invention may comprise a combination of Lactobacillus and Bifidobacterium. The most preferred Lactobacillus strain is the Lactobacillus rhamnosus GG strain available under the deposit number CGMCC 1.3724. The most preferred Bifidobacterium strain is the Bifidobacterium lactis BB12 strain deposited as CNCM 1-3446. Preferably the probiotics comprise a mixture of the Lactobacillus rhamnosus GG strain available under the deposit number CGMCC 1.3724 and of the Bifidobacterium lactis BB12 strain deposited as CNCM 1-3446. Most preferably the probiotics consist of a mixture of the Lactobacillus rhamnosus GG strain available under the deposit number CGMCC 1.3724 and of the Bifidobacterium lactis BB12 strain deposited as CNCM 1-3446. In a preferred embodiment, the probiotic is provided in an amount of from $10^5$ to $10^{12}$ colony forming units (cfu) per daily dose, more preferably from $10^7$ to $10^{11}$ cfu per daily dose.

The composition used for the purpose of the present invention may further comprise a combination of vitamins. For example, the composition may comprise at least one vitamin selected from the group consisting of vitamin B2, vitamin B6, vitamin B12, vitamin D and mixtures thereof. For example, the composition comprises vitamin B2, vitamin B6, vitamin B12 and vitamin D. Preferably the vitamin D is vitamin D3.

The present inventors were able to show (Crozier S R et al, Am J Clin Nutr. 2012; 96:57-63; Godfrey K M et al, Diabetes. 2011; 60:1528-34; Childs C et al., J Dev Orig Health Dis. 2015; 6(Suppl 2):536; that pregnant women were more often deficient in vitamins B6, B12 and D compared to other nutrients. Also, they have demonstrated that vitamin B2 was not consumed in sufficient amounts by a significant proportion of the pregnant woman population. It is therefore of particular interest to supplement the diet of pregnant women with these vitamins in order to compensate these particularly often-occurring deficiencies.

If present, the vitamin B2 is preferably provided in an amount of from 0.14 to 14 mg per daily dose. If present, the vitamin B6 is preferably provided in an amount of from 0.19 to 19 mg per daily dose. If present, the vitamin B12 is preferably provided in an amount of from 0.26 to 26 µg per daily dose. If present, the vitamin D is preferably provided in an amount of from 1.5 to 100 µg per daily dose. Most preferably, the composition for use in accordance with the present invention comprises 1.8 mg of vitamin B2, 2.6 mg of vitamin B6, 5.2 µg of vitamin B12 and 10 µg of vitamin D per daily dose.

In one embodiment of the present invention, the composition for use in accordance with the present invention comprises myo-inositol, vitamin B2, vitamin B6, vitamin B12, vitamin D, *Bifidobacterium lactis* BB12 CNCMI-3446 and *Lactobacillus rhamnosus* GG CGMCC 1.3724. For example, the composition for use in accordance with the present invention may comprise from 0.2 to 5 g of myo-inositol, from 0.14 to 14 mg of vitamin B2, from 0.19 to 19 mg of vitamin B6, from 0.26 to 26 µg of vitamin B12, from 1.5 to 100 µg of vitamin D, from $10^5$ to $10^{12}$ cfu of *Bifidobacterium lactis* BB12 CNCMI-3446 and a from $10^5$ to $10^{12}$ cfu of *Lactobacillus rhamnosus* GG CGMCC 1.3724, all amounts being defined by daily dose.

The inventors have also provided evidence (Patent No. 14719) of common zinc deficiencies in at least certain populations of pregnant woman, even though in a lesser extent than vitamins B2, B12, B6 and D. It is therefore also particularly advantageous to supplement the diet of pregnant women with zinc. Thus, the composition for use in accordance with the present invention may comprise zinc. Zinc may be present in an amount of from 1.1 to 40 mg per daily dose.

Additional vitamins and minerals may also be added. For example, vitamins and minerals may be added in accordance with the recommendations of Government bodies such as the USRDA. For example, the composition may contain one or more of the following micronutrients, calcium, magnesium, phosphorus, iron, zinc, copper, iodine, selenium, vitamin A or retinol activity equivalent (RAE) for example in the form of beta carotene or a mix of carotenoids, Vitamin C, Vitamin B1, niacin, folic acid, biotin, Vitamin E. Preferably the composition may contain one or more of the following micronutrients in the following amounts: 100 to 2500 mg calcium, 35 to 350 mg magnesium, 70 to 3500 mg phosphorus, 2.7 to 45 mg iron, 1.1 to 40 mg zinc, 0.1 to 10 mg copper, 22 to 1,100 µg iodine, 6 to 400 µg selenium, 77 to 3000 µg of vitamin A or retinol activity equivalent (RAE) for example in the form of beta carotene or a mix of carotenoids, 8.5 to 850 mg Vitamin C, 0.14 to 14 mg Vitamin B1, 1.8 to 35 mg niacin, 60 to 1000 µg folic acid, 3 to 300 µg biotin, 1.9 to 109 µg Vitamin E.

The composition for use in accordance with the present invention may advantageously further comprise at least one oil selected from long chain polyunsaturated fatty acids, such as arachidonic acid (ARA), eicosapentaenoic acid (EPA) and/or docosahexaenoic acid (DHA), in any suitable amount as known by the person skilled in the art, for example in an amount of 100-500 mg per daily dose, more preferably between 200 and 400 mg per daily dose.

Any of the nutrients mentioned herein may be used in any amount that is effective in achieving the objective of the present invention. Skilled artisans will be able to determine appropriate dosages. Typically, dosage will depend on age, size and health status of the mother, on her lifestyle, as well as on her genetic heritage.

Typically, amounts are defined in the present application as amounts per daily dose. The amount of nutrient may thus be selected in each composition accordingly depending upon whether it is intended to be consumed once a day or more or less frequently.

The nutrients may be provided as a sustained release formulation. This way, the nutrient can be consumed less frequently, while the body is still constantly supplied with sufficient amount of such nutrient.

The composition of the present invention may be intended for maternal administration. This means that the composition may to be administered to a female desiring to get pregnant, or to a pregnant female. The composition may be to be administered to a woman desiring to get pregnant, or to a pregnant woman. Preferably, the composition for use in accordance with the present invention is to be administered to a woman desiring to get pregnant and/or to a pregnant woman, most preferably to a pregnant woman.

The composition for use in accordance with the present invention may be to be administered to a woman desiring to get pregnant, for example during at least 1, 2, 3 or 4 months preceding the pregnancy or desired pregnancy. When the composition is to be administered to a pregnant woman, the composition is preferably administered for at least 4, preferably at least 8, more preferably at least 12, more preferably at least 16, more preferably at least 20, more preferably at least 24, more preferably at least 28, even more preferably at least 36 weeks during pregnancy. As the nutritional requirements increase in the second and third trimester of pregnancy, it is further preferred to administer the composition for use in accordance with the present invention throughout the third trimester of pregnancy and most preferably throughout the second and third trimesters of pregnancy.

It is important that women desiring to get pregnant prepare their body for the pregnancy by taking appropriate nutrients. Then, women's nutrients need increases during pregnancy. The composition for use in accordance with the present invention is specifically designed to meet the needs of the woman during this period.

In an embodiment of the present invention, the composition for use in accordance with the present invention may be to be administered to a subject at risk of premature delivery and/or PPROM.

Subjects at risk of PPROM are well known to the skilled artisan. For example, women are at risk of PPROM if they have a previous history of PPROM, are smokers, or have a cervical cerclage. For example, women may also be at risk are at risk of PPROM if they have a have a genital tract infection, previous uterine instrumentation and/or previous cervical surgery/trauma.

Subjects at risk of premature delivery are also well known to the person skilled in the art and include subjects that have had a premature baby in the past, subjects that are pregnant with multiples, subjects with abnormalities in the uterus or cervix, subjects that are underweight or overweight before pregnancy, and subjects with a family history of premature birth.

The composition can be in any form that is suitable to administer all the ingredients. For example, it can be in the form of a powdered nutritional composition to be reconstituted in milk or water, a food product, a drink, a nutritional supplement or a nutraceutical.

When the composition is in the form of a powdered nutritional composition to be reconstituted in milk or water it preferably comprises a protein source, a carbohydrate source and a lipid source, preferably together with lecithin. It may also comprise soya lecithin and/or a bulking agent. The protein source may be dried milk or dried skimmed milk. As carbohydrate source sucrose and/or maltodextrin may be used. The lipid source may be vegetable oil. The formulation may also alternatively or additionally contain glucose syrup, milk fat, magnesium citrate, choline salts and esters, prebiotic fibers, and/or ascorbyl palmitate. Flavor compounds, such as cocoa powder or honey, for example, may be added to provide taste variations.

The composition may be any type of composition suitable for consumption for the subject to whom it is to be administered.

The composition may also be a product selected from the group consisting of a nutritional product, a functional food product, a healthy ageing product, a dairy product, a dairy alternative product, a beverage product, a diet product, and a pet food product.

The term "nutritional product", as used herein, means any product that can be used to provide nutrition to a subject. Typically, nutritional products contain a protein source, a carbohydrate source and a lipid source.

The term "food product", as used herein, refers to any kind of product that may be safely consumed by a human or an animal. Said food product may be in solid, semi-solid or liquid form and may comprise one or more nutrients, foods or nutritional supplements. For instance, the food product may additionally comprise the following nutrients and micronutrients: a source of proteins, a source of lipids, a source of carbohydrates, vitamins and minerals. The composition may also contain anti-oxidants, stabilizers (when provided in solid form) or emulsifiers (when provided in liquid form).

The term "functional food product", as used herein, refers to a food product providing an additional health-promoting or disease-preventing function to the individual.

The term "healthy ageing product", as used herein, refers to a product providing an additional health-promoting or disease-preventing function related to healthy ageing to the individual.

The term "dairy products", as used herein, refers to food products produced from milk or fractions of milk from animals such as cows, goats, sheep, yaks, horses, camels, and other mammals. Examples of dairy products are low fat milk (e.g. 0.1%, 0.5% or 1.5% fat), fat-free milk, milk powder, whole milk, whole milk products, butter, butter-milk, buttermilk products, skim milk, skim milk products, high milk-fat products, condensed milk, crème fraiche, cheese, ice cream and confectionery products, probiotic drinks or probiotic yoghurt type drinks.

The term "dairy alternative product" refers to products similar to dairy products but produced without milk.

The term "milk" is defined by Codex Alimentarius as the normal mammary secretion of milking animals obtained from one or more milkings without either addition to it or extraction from it, intended for consumption as liquid milk or for further processing.

The term "beverage product" as used herein, refers to a nutritional product in liquid or semi-liquid form that may be safely consumed by an individual.

The term "diet product" as used herein, refers to a food product with a restricted and/or reduced caloric content.

The term "pet food product" as used herein refers to a nutritional product that is intended for consumption by pets. A pet, or companion animal, as referenced herein, is to be understood as an animal selected from dogs, cats, birds, fish, rodents such as mice, rats The term "nutritional supplement" as used herein, refers to a nutritional product that provides nutrients to an individual that may otherwise not be consumed in sufficient quantities by said individual. For instance, a nutritional supplement may include vitamins, minerals, fiber, fatty acids, or amino acids. Nutritional supplements may for example be provided in the form of a pill, a tablet, a lozenge, a chewy capsule or tablet, a tablet or capsule, or a powder supplement that can for example be dissolved in water or sprinkled on food. Nutritional supplements typically provide selected nutrients while not representing a significant portion of the overall nutritional needs of a subject. Typically, they do not represent more than 0.1%, 1%, 5%, 10% or 20% of the daily energy need of a subject. A nutritional supplement may be used during pregnancy, e.g., as a maternal supplement.

All ingredients of the composition can be admixed together or alternatively the composition can be provided in the form of a kit of parts wherein ingredients or groups of ingredients are provided separately. These separate compositions may be intended to be consumed separately or together.

Therefore a kit of parts for use in the prevention of the prevention of preterm birth and/or of conditions linked to preterm delivery in a female subject and/or in the offspring in a female subject comprising at least two physically separated compositions each comprising at least one of the ingredients mentioned above, wherein at least one of the physically separated compositions comprises myo-inositol and at least one of the physically separated compositions comprises probiotics, is another object of the present invention.

Hence, the present invention further concerns a kit of parts comprising at least two physically separated compositions, each comprising at least one ingredient selected from the group consisting of from vitamin B2, vitamin B6, vitamin B12, and vitamin D, at least one of the physically separated compositions comprises myo-inositol and at least one of the physically separated compositions comprises probiotics, for use in the prevention of preterm birth and/or of conditions linked to preterm delivery in a female subject and/or in the offspring. In one embodiment, the kits of parts is for use in the prevention of preterm delivery via prevention of PPROM in a female subject.

Therefore a kit of parts for use in the prevention of a of preterm-onset pre-labour rupture of membranes (PPROM) and disorders and/or conditions linked to PPROM in a female subject comprising at least two physically separated compositions each comprising at least one of the ingredients mentioned above, wherein at least one of the physically separated compositions comprises myo-inositol and at least one of the physically separated compositions comprises probiotics, is another object of the present invention.

Hence, the present invention also concerns a kit of parts comprising at least two physically separated compositions, each comprising at least one ingredient selected from the group consisting of from vitamin B2, vitamin B6, vitamin B12, and vitamin D, at least one of the physically separated compositions comprises myo-inositol and at least one of the physically separated compositions comprises probiotics, for use in the prevention of a of preterm-onset pre-labour rupture of membranes (PPROM) and disorders and/or conditions linked to PPROM in a female subject.

Each of the physically separated compositions can further comprise one or more of the other ingredients mentioned above. Most preferably, a first composition comprises at least one vitamin selected from vitamin B2, vitamin B6, vitamin B12, vitamin D and mixtures thereof and a second composition comprises probiotics. Myo-inositol can be provided in the first or the second composition or even separately, but is preferably provided in the same composition as the vitamins. In a preferred embodiment of the invention, the kit of parts comprises a first composition comprising myo-inositol and at least one vitamin selected from vitamin B2, vitamin B6, vitamin B12, vitamin D and mixtures thereof, optionally with other vitamins and/or nutrients mentioned above, except probiotics, and a second composition comprising probiotics. In a most preferred embodiment, the kit of parts comprises a first composition comprising myo-inositol, vitamin B2, vitamin B6, vitamin B12, vitamin D and zinc and a second composition comprising probiotics. Separation of probiotics from other ingredients is mostly preferred to avoid any damage to the probiotics due to the presence of high concentration of minerals or other nutrients.

For the purpose of the present invention, the composition (or the compositions contained in the kit of part) is administered regularly, for example two times a day, daily, every two days or weekly.

Those skilled in the art will understand that they can freely combine all features of the present invention disclosed herein. In particular, features described for the composition for use of the present invention may be combined with the kit of parts for use of the present invention and vice versa. Further, features described for different embodiments of the present invention may be combined.

Although the invention has been described by way of example, it should be appreciated that variations and modifications may be made without departing from the scope of the invention as defined in the claims.

The term "and/or" used in the context of the "X and/or Y" should be interpreted as "X", or "Y", or "X and Y".

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 8, from 3 to 7, from 4 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

Unless defined otherwise, all technical and scientific terms used herein have the same meaning as commonly understood by one of ordinary skill in the art.

Furthermore, where known equivalents exist to specific features, such equivalents are incorporated as if specifically referred in this specification. Further advantages and features of the present invention are apparent from the figures and non-limiting examples.

EXAMPLES

Example 1

A nutritional supplement in powder form intended to be dissolved in water is provided with the ingredients as shown in FIG. 1.

*Lactobacillus rhamnosus* GG was deposited as CGMCC 1.3724.

*Bifidobacterium lactis* BB12 was deposited as CNCM 1-3446.

The composition is provided as one sachet containing the probiotic and all other ingredients as a powder. The composition was administered to women desiring to get pregnant during at least one month prior to pregnancy and later to the same woman until delivery.

Example 2

Five hundred eighty-five women participating in the NiP-PeR trial (Godfrey K M et al; Trials (2017), 18: 131) across three clinical sites were included in the analyses. This included 295 in the intervention and 290 in the control group. On average, women were 30 years of age, at the upper end of the normal weight range, and predominantly nulliparous. European and Chinese ethnicities accounted for >80% of ethnicities.

As shown in FIG. 5, the nutritional intervention was associated with a significant reduction in the overall rate of preterm delivery when adjustment was made for covariates including site and ethnicity ("basic model"), and additionally for site and ethnicity, offspring's sex, maternal age, educational/income level, parity, smoking during pregnancy, maternal pre-conception BMI, glycemia (fasting glucose at pregnancy week 28)("adjusted model" FIG. 5). A greater reduction (52% less odds compared to 76%) was observed in the overweight/obese women subset (defined using ethnic specific thresholds, i.e. body mass index>23 kg/m2 for Asians, >25 kg/m2 for non-Asians including White Caucasian, Polynesian, Black), when adjusting for the same covariates.

As shown in FIG. 2, the nutritional intervention also led to a statistically significant reduction in PPROM when adjustment was made for covariates including site and ethnicity ("basic model" in FIGS. 2, 3, 4 and 5), and additional for offspring's sex, maternal age, educational/income level, parity, smoking during pregnancy, maternal pre-conception BMI, glycemia (preconception fasting glucose)("adjusted model" FIG. 2). A clear trend in the same direction was observed also when the same statistical analysis was carried out on a sample population whereby stillbirths were excluded and fasting glucose at pregnancy week 28 was used in the adjustment (FIG. 2bis).

PPROM is a well recognised risk factor for preterm delivery. Subsequent analysis found a lower incidence of preterm delivery associated with PPROM in the nutritional intervention group than in the control group. The results are shown in FIG. 3. Also in this case, adjustment was made for covariates including site and ethnicity ("basic model"), and additional for offspring's sex, maternal age, educational/income level, parity, smoking during pregnancy, maternal pre-conception BMI, glycemia (fasting glucose at pregnancy week 28)("adjusted model")

A similar trend for lower incidence of preterm delivery associated with PPROM was seen in both spontaneous and non-spontaneous preterm delivery groups (FIG. 4), i.e. the protection against preterm delivery provided by the nutritional intervention according to the present invention appears to be driven by an association with PPROM. Adjustment was made for covariates including site and ethnicity ("basic model").

Additionally, it was shown that following the occurrence of PPROM the timing of delivery was more likely to be at term than preterm (before 37 weeks) in the intervention group (FIG. 6).

EMBODIMENTS OF THE PRESENT INVENTION a) Composition comprising myo-inositol for use in the prevention of a preterm-onset pre-labour rupture of membranes (PPROM) and disorders and/or conditions linked to PPROM in a female subject.

b) Composition for use in accordance with embodiment a), wherein the composition further comprises probiotics.

c) Composition for use in accordance with embodiment b), wherein the probiotics comprise a combination of *Lactobacillus* and *Bifidobacterium*.

d) Composition for use in accordance with embodiment c), wherein the *Lactobacillus* is the *Lactobacillus rhamnosus* GG strain available under the deposit number CGMCC 1.3724, and the *Bifidobacterium* is the *Bifidobacterium lactis* BB12 strain deposited as CNCM 1-3446.

e) Composition for use in accordance with one of the preceding embodiments, wherein the composition further comprises at least one vitamin selected from the group consisting of vitamin B2, vitamin B6, vitamin B12, vitamin D and mixtures thereof.

f) Composition for use in accordance with one of the preceding embodiments, wherein the composition comprises myo-inositol, vitamin B2, vitamin B6, vitamin B12, vitamin D, a *Bifidobacterium lactis* BB12 CNCMI-3446 and a *Lactobacillus rhamnosus* GG CGMCC 1.3724.

g) Composition for use in accordance with one of the preceding embodiments, wherein the composition comprises 0.2 to 5 g of myo-inositol, from 0.14 to 14 mg of vitamin B2, from 0.19 to 19 mg of vitamin B6, from 0.26 to 26 μg of vitamin B12, from 1.5 to 100 μg of vitamin D, from $10^5$ to $10^{12}$ cfu of *Bifidobacterium lactis* BB12 CNCMI-3446 and a from $10^5$ to $10^{12}$ cfu of *Lactobacillus rhamnosus* GG CGMCC 1.3724, all amounts being defined by daily dose.

h) Composition for use in accordance with one of the preceding embodiments, wherein the composition further comprises zinc.

i) Composition for use in accordance with one of the preceding embodiments, wherein the disorder and/or condition linked to a PPROM is selected from the group consisting of premature birth; infections, such as infections of the amniotic fluid and membranes, for example; the separation of the placenta from the uterus;

complications with the umbilical cord; the necessity to deliver by surgical or cesarean section and combinations thereof.

j) Composition for use in accordance with one of the preceding embodiments, wherein the subject is a mammal, for example selected from the group consisting of a cat, a dog and a human.

k) Composition for use in accordance with one of the preceding embodiments, wherein the subject is a female who is trying to get pregnant or is pregnant.

l) Composition for use in accordance with one of the preceding embodiments, wherein the composition is to be administered to a subject at risk of premature delivery and/or PPROM.

m) Composition for use in accordance with one of the preceding embodiments, wherein the composition is to be administered to a subject during pregnancy, for example during throughout the second and third trimesters of pregnancy.

n) Composition for use in accordance with one of the preceding embodiments, wherein the composition is in the form of a powdered nutritional composition to be reconstituted in milk or water, a food product, a drink, a nutritional supplement or a nutraceutical.

o) A kit of parts comprising at least two physically separated compositions, each comprising at least one ingredient selected from the group consisting of from vitamin B2, vitamin B6, vitamin B12, and vitamin D, at least one of the physically separated compositions comprises myo-inositol and at least one of the physically separated compositions comprises probiotics, for use in the prevention of a of preterm-onset pre-labour rupture of membranes (PPROM) and disorders and/or conditions linked to PPROM in a female subject.

The invention claimed is:

1. A method for reducing risk of preterm birth and/or of a condition linked to preterm birth in a female subject and/or in offspring of the female subject, the method comprising administering to the female subject a composition comprising myo-inositol,
   wherein the female subject is at risk of preterm-onset pre-labour rupture of membranes (PPROM) and had a previous history of PPROM.

2. The method in accordance with claim 1, wherein the composition further comprises probiotics.

3. The method in accordance with claim 2, wherein the probiotics comprise a combination of *Lactobacillus* and *Bifidobacterium*.

4. The method in accordance with claim 3, wherein the *Lactobacillus* is the *Lactobacillus rhamnosus* GG strain available under the deposit number CGMCC 1.3724, and the *Bifidobacterium* is the *Bifidobacterium lactis* BB12 strain deposited as CNCM I-3446.

5. The method in accordance with claim 1, wherein the composition further comprises at least one vitamin selected from the group consisting of vitamin B2, vitamin B6, vitamin B12, vitamin D and mixtures thereof.

6. The method in accordance with claim 1, wherein the composition comprises the myo-inositol, vitamin B2, vitamin B6, vitamin B12, vitamin D, a *Bifidobacterium lactis* BB12 CNCMI-3446 and a *Lactobacillus rhamnosus* GG CGMCC 1.3724.

7. The method in accordance with claim 1, wherein the composition comprises from 0.2 to 5 g of the myo-inositol, from 0.14 to 14 mg of vitamin B2, from 0.19 to 19 mg of vitamin B6, from 0.26 to 26 μg of vitamin B12, from 1.5 to 100 μg of vitamin D, from $10^5$ to $10^{12}$ cfu of *Bifidobacterium*

15

*lactis* BB12 CNCMI-3446 and from $10^5$ to $10^{12}$ cfu of *Lactobacillus rhamnosus* GG CGMCC 1.3724, all amounts being defined by daily dose.

8. The method in accordance with claim 1, wherein the composition further comprises zinc.

9. The method in accordance with claim 1, wherein the condition linked to preterm birth in the offspring of the female subject is selected from the group consisting of increased risk of neonatal respiratory conditions, necrotizing enterocolitis, sepsis, neurological conditions, feeding difficulties, visual and hearing problems, poor neurodevelopmental outcomes, high rates of hospital admissions, behavioral, social-emotional, learning difficulties in childhood, increased risks of hypertension later in life, cardiovascular and cerebrovascular diseases later in life, type 2 diabetes later in life, chronic kidney disease later in life, asthma and abnormalities in pulmonary function, neurocognitive disorder, and combinations thereof.

10. The method in accordance with claim 1, wherein the female subject is a mammal.

11. The method in accordance with claim 1, wherein the female subject is a female who is trying to get pregnant or is pregnant.

12. The method in accordance with claim 1, wherein the female subject is at risk of premature delivery.

13. The method in accordance with claim 1, wherein the composition is administered to the female subject during pregnancy.

14. The method in accordance with claim 1, wherein the composition is in a form selected from the group consisting of a powdered nutritional composition to be reconstituted in milk or water, a food product, a drink, a nutritional supplement, and a nutraceutical.

15. A method for reducing risk of preterm delivery and/or conditions linked to preterm delivery in a female subject and/or in offspring of the female subject, the method comprising providing to the female subject a kit comprising at least two physically separated compositions, each comprising at least one ingredient selected from the group consisting of vitamin B2, vitamin B6, vitamin B12, and vitamin D, wherein at least one of the physically separated compositions comprises myo-inositol and at least one of the physically separated compositions comprises probiotics, wherein the female subject is at risk of preterm-onset pre-labour rupture of membranes (PPROM) and had a previous history of PPROM.

16. The method in accordance with claim 9, wherein the neonatal respiratory conditions comprise at least one of respiratory distress syndrome or bronchopulmonary dysplasia.

17. The method in accordance with claim 9, wherein the neurological conditions comprise at least one of periventricular leukomalacia, seizures, intraventricular hemorrhage, cerebral palsy, or hypoxic ischemic encephalopathy.

* * * * *